United States Patent
Roelofszen et al.

(10) Patent No.: US 10,526,269 B2
(45) Date of Patent: *Jan. 7, 2020

(54) PROCESS OF ALKANE OXIDATIVE DEHYDROGENATION AND/OR ALKENE OXIDATION

(71) Applicant: SHELL OIL COMPANY, Houston, TX (US)

(72) Inventors: Dennis Petrus Maria Roelofszen, Amsterdam (NL); Guus Van Rossum, Amsterdam (NL); Ronald Jan Schoonebeek, Amsterdam (NL); Michael Johannes Franciscus Maria Verhaak, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/301,807

(22) PCT Filed: May 18, 2017

(86) PCT No.: PCT/EP2017/061954
§ 371 (c)(1),
(2) Date: Nov. 15, 2018

(87) PCT Pub. No.: WO2017/198762
PCT Pub. Date: Nov. 23, 2017

(65) Prior Publication Data
US 2019/0161427 A1    May 30, 2019

(30) Foreign Application Priority Data

May 19, 2016 (EP) .................................. 16170344

(51) Int. Cl.
| | | |
|---|---|---|
| *C07C 51/25* | (2006.01) | |
| *B01J 23/00* | (2006.01) | |
| *B01J 23/28* | (2006.01) | |
| *B01J 37/03* | (2006.01) | |
| *B01J 27/057* | (2006.01) | |
| *C07C 5/48* | (2006.01) | |
| *B01J 37/00* | (2006.01) | |
| *C07C 51/215* | (2006.01) | |
| *C07C 53/08* | (2006.01) | |
| *C07C 53/122* | (2006.01) | |
| *C07C 57/04* | (2006.01) | |

(52) U.S. Cl.
CPC ........... *C07C 51/252* (2013.01); *B01J 23/002* (2013.01); *B01J 23/28* (2013.01); *B01J 27/0576* (2013.01); *B01J 37/0045* (2013.01); *B01J 37/03* (2013.01); *C07C 5/48* (2013.01); *C07C 51/215* (2013.01); *C07C 51/25* (2013.01); *B01J 2523/00* (2013.01); *B01J 2523/55* (2013.01); *B01J 2523/56* (2013.01); *B01J 2523/64* (2013.01); *B01J 2523/68* (2013.01); *C07C 53/08* (2013.01); *C07C 53/122* (2013.01); *C07C 57/04* (2013.01); *C07C 2523/20* (2013.01); *C07C 2523/22* (2013.01); *C07C 2523/28* (2013.01); *C07C 2527/057* (2013.01); *Y02P 20/52* (2015.11)

(58) Field of Classification Search
CPC ....... C07C 5/48; C07C 11/04; C07C 2523/28; C07C 2523/847; C07C 2527/057; B01J 2523/00; B01J 2523/55; B01J 2523/56; B01J 2523/68

See application file for complete search history.

(56) References Cited

U.S. PATENT DOCUMENTS

| | | |
|---|---|---|
| 4,524,236 A | 6/1985 | McCain |
| 7,091,377 B2 | 8/2006 | Borgmeier et al. |
| 8,519,210 B2 † | 8/2013 | Arnold |
| 2002/0082445 A1 * | 6/2002 | Ellis .................. C07C 5/48 560/241.1 |
| 2004/0147393 A1 | 7/2004 | Hibst et al. |
| 2010/0256432 A1 | 10/2010 | Arnold et al. |
| 2015/0119622 A1 † | 4/2015 | De Rooij et al. |

FOREIGN PATENT DOCUMENTS

| | | |
|---|---|---|
| WO | 2003064035 A1 | 8/2003 |
| WO | 2010096909 A1 | 9/2010 |
| WO | 2014154808 A1 | 10/2014 |

OTHER PUBLICATIONS

International Search Report and Written Opinion received for PCT Patent Application No. PCT/EP2017/061954, dated Jul. 5, 2017, 8 pages.

\* cited by examiner
† cited by third party

*Primary Examiner* — Jafar F Parsa

(57) ABSTRACT

The invention relates to a process of the oxidative dehydrogenation of an alkane containing 2 to 6 carbon atoms and/or the oxidation of an alkene containing 2 to 6 carbon atoms, wherein oxygen, water and the alkane and/or alkene are fed to a reactor and are contacted with a mixed metal oxide catalyst containing molybdenum, vanadium, niobium and optionally tellurium in the reactor, and wherein the molar ratio of water as fed to the reactor to oxygen as fed to the reactor is smaller than 1:1.

4 Claims, No Drawings

PROCESS OF ALKANE OXIDATIVE DEHYDROGENATION AND/OR ALKENE OXIDATION

CROSS REFERENCE TO RELATED APPLICATIONS

This is a national stage application of International Application No. PCT/EP2017/061954, filed 18 May 2017, which claims benefit of priority to European Patent Application No. 16170344.2, filed 19 May 2016.

FIELD OF THE INVENTION

The present invention relates to a process of alkane oxidative dehydrogenation (oxydehydrogenation; ODH) and/or alkene oxidation.

BACKGROUND OF THE INVENTION

It is known to oxidatively dehydrogenate alkanes, such as alkanes containing 2 to 6 carbon atoms, for example ethane or propane resulting in ethylene and propylene, respectively, in an oxidative dehydrogenation (oxydehydrogenation; ODH) process. Examples of alkane ODH processes, including catalysts and other process conditions, are for example disclosed in U.S. Pat. No. 7,091,377, WO2003064035, US20040147393, WO2010096909 and US20100256432. Mixed metal oxide catalysts containing molybdenum (Mo), vanadium (V), niobium (Nb) and optionally tellurium (Te) as the metals, can be used as such oxydehydrogenation catalysts. Such catalysts may also be used in the direct oxidation of alkenes to carboxylic acids, such as in the oxidation of alkenes containing 2 to 6 carbon atoms, for example ethylene or propylene resulting in acetic acid and acrylic acid, respectively.

It is an objective of the present invention to provide a process of alkane oxidative dehydrogenation and/or alkene oxidation, using a mixed metal oxide catalyst containing Mo, V, Nb and optionally Te, wherein the catalyst activity and/or selectivity and/or stability may be maintained or even increased.

SUMMARY OF THE INVENTION

Surprisingly it was found that such alkane ODH and/or alkene oxidation process resulting in one or more of the above-mentioned improved properties, may be a process wherein the catalyst is contacted with oxygen, water and the alkane and/or alkene as fed to a reactor which contains the catalyst, wherein the molar ratio of water as fed to the reactor to oxygen as fed to the reactor is smaller than 1:1.

Accordingly, the present invention relates to a process of the oxidative dehydrogenation of an alkane containing 2 to 6 carbon atoms and/or the oxidation of an alkene containing 2 to 6 carbon atoms, wherein oxygen, water and the alkane and/or alkene are fed to a reactor and are contacted with a mixed metal oxide catalyst containing molybdenum, vanadium, niobium and optionally tellurium in the reactor, and wherein the molar ratio of water as fed to the reactor to oxygen as fed to the reactor is smaller than 1:1.

DETAILED DESCRIPTION OF THE INVENTION

While the process of the present invention and a stream or catalyst used in said process are described in terms of "comprising", "containing" or "including" one or more various described steps or components, they can also "consist essentially of" or "consist of" said one or more various described steps or components.

In the context of the present invention, in a case where a stream or catalyst comprises two or more components, these components are to be selected in an overall amount not to exceed 100 vol. % or 100 wt. %.

Within the present specification, by "substantially no" in relation to the amount of a specific component in a stream, it is meant an amount which is at most 1,000, preferably at most 500, more preferably at most 100, more preferably at most 50, more preferably at most 30, more preferably at most 20, and most preferably at most 10 ppmv (parts per million by volume) of the component in question, based on the amount (i.e. volume) of said stream.

In the process of the present invention, 1) oxygen ($O_2$), 2) water ($H_2O$) and 3) an alkane containing 2 to 6 carbon atoms and/or alkene containing 2 to 6 carbon atoms are fed to a reactor. Further, said reactor contains a mixed metal oxide catalyst containing molybdenum, vanadium, niobium and optionally tellurium. Said 3 components, that is to say oxygen, water and the alkane and/or alkene, are then contacted with said catalyst in the reactor, resulting in oxidative dehydrogenation (ODH) of the alkane and/or oxidation of the alkene.

Further, in the process of the present invention, the molar ratio of water as fed to the reactor to oxygen as fed to the reactor should be smaller than 1:1. The present inventors have surprisingly found that when using only a relatively small amount of water in the total feed to the reactor, as compared to the amount of oxygen which is fed to drive the alkane ODH and/or alkene oxidation reaction(s), the activity and/or selectivity and/or stability of the mixed metal oxide catalyst containing molybdenum, vanadium, niobium and optionally tellurium may be maintained or even increased. Further reference is made to the below-included Examples. One important advantage of using a catalyst which remains active and/or stable over time, is that there is no need for a frequent catalyst replacement (for example every few weeks or months) which would come at a high cost, in terms of catalyst consumption cost and downtime of the reactor.

WO2010115108 discloses a process for the oxidative dehydrogenation of ethane to ethylene, comprising contacting an ethane feed and an oxygen-containing gas in the presence of an oxidative dehydrogenation catalyst in an oxidative dehydrogenation reaction zone, wherein at least one of water and steam may be fed to the oxidative dehydrogenation reaction zone, as exemplified by feeds 10 in the Figures of WO2010115108. According to WO2010115108, the use of steam (or water) is optional. It is disclosed therein that steam may be provided in sufficient quantity to act as a heat diluent, limiting reaction temperature rise, and hot spots, and to avoid formation of a flammable feed mixture. Subsequent to that, typical feed compositions comprising ethane, oxygen and water (steam) at different ethane conversion levels are disclosed in WO2010115108.

In WO2010115108, the amount of water is relatively large as compared to the amount of oxygen. Furthermore, according to WO2010115108, the amount of water is dependent on the desired ethane conversion (per pass). The higher said conversion is, the more water relative to oxygen needs to be used. For example, at an ethane conversion of 70% the molar ratio of water to oxygen is about 10:1 (that is to say, 77:8) whereas at an ethane conversion of 30% the molar ratio of water to oxygen is only 1:1 (that is to say, 15:15). In Feeds A and B as used in the Examples of WO2010115108, the molar ratio of water to oxygen is also 1:1 (that is to say, 10:10).

WO2010115108 does not disclose or suggest to feed water (steam) to a reactor in order to maintain or increase the activity and/or selectivity and/or stability of a mixed metal oxide catalyst containing molybdenum, vanadium, niobium and optionally tellurium used for alkane ODH and/or alkene oxidation. In WO2010115108, water is added in relatively high amounts for other purposes.

In the alkane oxidative dehydrogenation process and/or alkene oxidation process of the present invention, 1) oxygen ($O_2$), 2) water ($H_2O$) and 3) an alkane containing 2 to 6 carbon atoms and/or alkene containing 2 to 6 carbon atoms are fed to the reactor. Said components may be fed to the reactor together or separately. That is to say, one or more feed streams, suitably gas streams, comprising one or more of said 3 components may be fed to the reactor. For example, one feed stream comprising oxygen, water and the alkane and/or alkene may be fed to the reactor. Alternatively, two or more feed streams, suitably gas streams, may be fed to the reactor, which feed streams may form a combined stream inside the reactor. For example, one feed stream comprising water and another feed stream comprising oxygen and the alkane and/or alkene may be fed to the reactor separately.

Further, irrespective of whether oxygen, water and the alkane containing 2 to 6 carbon atoms and/or alkene containing 2 to 6 carbon atoms are fed to the reactor together or separately in the same or different feed streams as described above, said components are suitably fed to the reactor simultaneously (at the same time).

However, it is also envisaged that before and/or after feeding oxygen, water and the alkane and/or alkene to the reactor and contacting the oxygen, water and alkane and/or alkene with the catalyst in the reactor in accordance with the invention as described hereinbefore, oxygen and the alkane and/or alkene may be fed and contacted with the catalyst without feeding water to the reactor.

In the above-described case, the process of the present invention may comprise two or more of the following sequential steps, wherein the process should comprise (non-optional) step 2) wherein water is fed to the reactor and one or more of optional steps 1) and 3) wherein substantially no water is fed to the reactor:

1) optionally feeding oxygen and an alkane containing 2 to 6 carbon atoms and/or an alkene containing 2 to 6 carbon atoms to a reactor wherein substantially no water is fed to the reactor, and contacting the oxygen and alkane and/or alkene with a mixed metal oxide catalyst containing molybdenum, vanadium, niobium and optionally tellurium in the reactor; followed by 2) feeding oxygen, water and an alkane containing 2 to 6 carbon atoms and/or an alkene containing 2 to 6 carbon atoms to a reactor wherein the molar ratio of water as fed to the reactor to oxygen as fed to the reactor is smaller than 1:1, and contacting the oxygen, water and alkane and/or alkene with the above-described catalyst in the reactor; followed by 3) optionally feeding oxygen and an alkane containing 2 to 6 carbon atoms and/or an alkene containing 2 to 6 carbon atoms to a reactor wherein substantially no water is fed to the reactor, and contacting the oxygen and alkane and/or alkene with the above-described catalyst in the reactor.

Suitably, in the above-described case, the process of the present invention comprises above-described steps 1) and 2). By feeding water to the reactor in said step 2), the catalyst which may have become deactivated to some extent in the preceding step 1), may be reactivated and may then have a stable performance over time. Further, preferably, in the above-described case, the process of the present invention does not comprise above-described step 3).

Further, in the process of the present invention, once the feeding of water to the reactor has started, (i) either simultaneously with feeding oxygen and the alkane and/or alkene or (ii) together with oxygen and the alkane and/or alkene some time after the feeding of oxygen and the alkane and/or alkene to the reactor has started, such feeding of water to the reactor, together with feeding oxygen and the alkane and/or alkene to the reactor, is continued during the entire process.

In the process of the present invention, oxygen and the alkane containing 2 to 6 carbon atoms and/or alkene containing 2 to 6 carbon atoms are suitably fed to the reactor in the gas phase. Further, in the process of the present invention, water may be fed to the reactor in the gas phase or in the liquid phase, suitably in the gas phase. In particular, water may be fed to the reactor as a steam which is in the gas phase which may be (i) water in the gas phase which is formed when water boils or (ii) water in the gas phase which is formed by passing a dry (water-unsaturated) stream containing oxygen and/or an inert gas through liquid water. Further, in particular, water may be fed to the reactor as a wet steam which is a mist or aerosol of water droplets formed as water vapor condenses. In case water is fed to the reactor in the liquid phase, the water suitably evaporates under the reaction conditions inside the reactor.

In the process of the present invention, the molar ratio of water as fed to the reactor to oxygen as fed to the reactor is smaller than 1:1. Naturally, the phrase "water as fed to the reactor" for example does not include water that is not fed to the reactor, such as water that may be formed during the alkane ODH and/or alkene oxidation reaction(s) that take place in the present process. As mentioned above, the water and oxygen may be fed to the reactor in the same feed stream or in different feed streams. Furthermore, each of the components may be fed to the reactor in two or more feed streams. Thus, the above-mentioned "molar ratio of water as fed to the reactor to oxygen as fed to the reactor" refers to the total molar amount of water as fed to the reactor relative to the total molar amount of oxygen as fed to the reactor.

In the process of the present invention, the molar ratio of water as fed to the reactor to oxygen as fed to the reactor is preferably of from 0.01:1 to smaller than 1:1, more preferably 0.1:1 to 0.8:1, most preferably 0.2:1 to 0.6:1. Said molar ratio may be at least 0.01, or at least 0.05:1, or at least 0.1:1, or at least 0.15:1, or at least 0.2:1, or at least 0.25:1, or at least 0.3:1, or at least 0.35:1, or at least 0.4:1. Further, said molar ratio is at most smaller than 1:1 and may be at most 0.9:1, or at most 0.8:1, or at most 0.75:1, or at most 0.7:1, or at most 0.65:1, or at most 0.6:1.

Further, in the process of the present invention, the total amount of water and oxygen as fed to the reactor, based on the total amount of components as fed to the reactor, is suitably of from 10 to 80 vol %, more suitably 15 to 70 vol. %, most suitably 20 to 60 vol. %. Said total amount may be at least 5 vol. %, or at least 10 vol. %, or at least 15 vol. %, or at least 20 vol. %, or at least 25 vol. %. Further, said total amount may be at most 90 vol. %, or at most 80 vol. %, or at most 70 vol. %, or at most 60 vol. %, or at most 50 vol. %, or at most 40 vol. %, or at most 35 vol. %, or at most 30 vol. %.

Still further, in the process of the present invention, the molar ratio of the total amount of water and oxygen as fed to the reactor to the alkane containing 2 to 6 carbon atoms and/or the alkene containing 2 to 6 carbon atoms as fed to the reactor is suitably of from 0.01:1 to smaller than 1:1, more suitably 0.1:1 to 0.8:1, most suitably 0.2:1 to 0.6:1. Said molar ratio may be at least 0.01, or at least 0.05:1, or at least 0.1:1, or at least 0.15:1, or at least 0.2:1, or at least 0.25:1, or at least 0.3:1, or at least 0.35:1, or at least 0.4:1. Further, said molar ratio is at most smaller than 1:1 and may be at most 0.9:1, or at most 0.8:1, or at most 0.75:1, or at most 0.7:1, or at most 0.65:1, or at most 0.6:1.

In the present invention, the conversion of the alkane containing 2 to 6 carbon atoms and/or the alkene containing 2 to 6 carbon atoms, as fed to the reactor, may vary widely. Suitably, said conversion is higher than 30%, or of from 35 to 95%, or of from 40 to 70%, or of from 45 to 55%. Suitably, said conversion is higher than 30%, more suitably at least 35%, more suitably at least 40%, most suitably at least 45%. Further, suitably, said conversion is at most 95%, more suitably at most 85%, more suitably at most 75%, more suitably at most 70%, more suitably at most 65%, more suitably at most 60%, most suitably at most 55%. By said "conversion", reference is made to a "conversion per pass" in the case of a reactor where unconverted reactant(s) is (are) recovered from the product stream and recycled to the reactor.

Preferably, in the present alkane oxidative dehydrogenation process and/or alkene oxidation process, that is to say during contacting the oxygen, water and the alkane and/or alkene with the catalyst, the temperature is of from 300 to 500° C. More preferably, said temperature is of from 310 to 450° C., more preferably of from 320 to 420° C., most preferably of from 330 to 420° C.

Still further, in the present alkane oxidative dehydrogenation process and/or alkene oxidation process, that is to say during contacting the oxygen, water and the alkane and/or alkene with the catalyst, typical pressures are 0.1-30 or 0.1-20 bara (i.e. "bar absolute"). Further, preferably, said pressure is of from 0.1 to 15 bara, more preferably of from 1 to 8 bara, most preferably of from 3 to 8 bara.

Preferably, in the alkane oxidative dehydrogenation process of the present invention, the alkane containing 2 to 6 carbon atoms is a linear alkane in which case said alkane may be selected from the group consisting of ethane, propane, butane, pentane and hexane. Further, preferably, said alkane contains 2 to 4 carbon atoms and is selected from the group consisting of ethane, propane and butane. More preferably, said alkane is ethane or propane. Most preferably, said alkane is ethane.

Further, preferably, in the alkene oxidation process of the present invention, the alkene containing 2 to 6 carbon atoms is a linear alkene in which case said alkene may be selected from the group consisting of ethylene, propylene, butene, pentene and hexene. Further, preferably, said alkene contains 2 to 4 carbon atoms and is selected from the group consisting of ethylene, propylene and butene. More preferably, said alkene is ethylene or propylene.

The product of said alkane oxidative dehydrogenation process may comprise the dehydrogenated equivalent of the alkane, that is to say the corresponding alkene. For example, in the case of ethane such product may comprise ethylene, in the case of propane such product may comprise propylene, and so on. Such dehydrogenated equivalent of the alkane is initially formed in said alkane oxidative dehydrogenation process. However, in said same process, said dehydrogenated equivalent may be further oxidized under the same conditions into the corresponding carboxylic acid which may or may not contain one or more unsaturated double carbon-carbon bonds. As mentioned above, it is preferred that the alkane containing 2 to 6 carbon atoms is ethane or propane. In the case of ethane, the product of said alkane oxidative dehydrogenation process may comprise ethylene and/or acetic acid, preferably ethylene. Further, in the case of propane, the product of said alkane oxidative dehydrogenation process may comprise propylene and/or acrylic acid, preferably acrylic acid.

The product of said alkene oxidation process comprises the oxidized equivalent of the alkene. Preferably, said oxidized equivalent of the alkene is the corresponding carboxylic acid. Said carboxylic acid may or may not contain one or more unsaturated double carbon-carbon bonds. As mentioned above, it is preferred that the alkene containing 2 to 6 carbon atoms is ethylene or propylene. In the case of ethylene, the product of said alkene oxidation process may comprise acetic acid. Further, in the case of propylene, the product of said alkene oxidation process may comprise acrylic acid.

In addition to oxygen, water and the alkane and/or alkene, an inert gas may also be fed. Said inert gas may be selected from the group consisting of the noble gases and nitrogen ($N_2$). Preferably, the inert gas is nitrogen or argon, more preferably nitrogen. Said oxygen is an oxidizing agent, thereby resulting in oxidative dehydrogenation of the alkane and/or oxidation of the alkene. Said oxygen may originate from any source, such as for example air. Ranges for the molar ratio of oxygen to the alkane and/or alkene which are suitable, are of from 0.01 to 1, more suitably 0.05 to 0.5. Said ratio of oxygen to the alkane and/or alkene is the ratio before oxygen and the alkane and/or alkene are contacted with the catalyst. In other words, said ratio of oxygen to the alkane and/or alkene is the ratio of oxygen as fed to the alkane and/or alkene as fed. Obviously, after contact with the catalyst, at least part of the oxygen and alkane and/or alkene gets consumed.

Preferably, in the present invention, the mixed metal oxide catalyst containing molybdenum, vanadium, niobium and optionally tellurium is a heterogeneous catalyst.

In the present invention, the catalyst is a mixed metal oxide catalyst containing molybdenum, vanadium, niobium and optionally tellurium as the metals, which catalyst may have the following formula:

$$Mo_1V_aTe_bNb_cO_n$$

wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for O) is a number which is determined by the valency and frequency of elements other than oxygen.

The amount of the catalyst in said process is not essential. Preferably, a catalytically effective amount of the catalyst is used, that is to say an amount sufficient to promote the alkane oxydehydrogenation and/or alkene oxidation reaction.

The reactor that may be used in the present process may be any reactor, including fixed-bed and fluidized-bed reactors. Suitably, the reactor is a fixed-bed reactor. In such case, oxygen, water and the alkane and/or alkene are fed to one or more inlets of the fixed-bed reactor and are contacted with a mixed metal oxide catalyst containing molybdenum, vanadium, niobium and optionally tellurium as contained in the catalyst bed in the fixed-bed reactor, wherein the molar ratio of water as fed to the reactor to oxygen as fed to the reactor is smaller than 1:1. Preferably, in such case, the water is fed to that part of the reactor and catalyst bed where the concentration of the alkane and/or alkene fed is still relatively high. For example, in a case where there is a flow comprising oxygen and the alkane and/or alkene which goes from the top to the bottom of a fixed-bed reactor, the water is preferably also fed to the top, suitably in a region which is at a distance of from 0 to 30% from the top relative to total reactor length (top to bottom).

In general, water is formed during the alkane ODH and/or alkene oxidation reaction(s) that take place in the present process, which water may end up in the product stream in addition to the desired product and in addition to water as fed to the reactor. Water may easily be separated from said product stream, for example by cooling down the product stream from the reaction temperature to a lower temperature, for example room temperature, so that the water condenses and can then be separated from the product stream.

Examples of oxydehydrogenation processes, including catalysts and process conditions, are for example disclosed in above-mentioned U.S. Pat. No. 7,091,377, WO2003064035, US20040147393, WO2010096909 and US20100256432, the disclosures of which are herein incorporated by reference.

The invention is further illustrated by the following Examples.

Examples (A) Preparation of the Catalyst

A mixed metal oxide catalyst containing molybdenum (Mo), vanadium (V), niobium (Nb) and tellurium (Te) was prepared, for which catalyst the molar ratio of said 4 metals was $Mo_1V_{0.29}Nb_{0.17}Te_{0.12}$.

Two solutions were prepared. Solution 1 was obtained by dissolving 15.8 g of ammonium niobate oxalate and 4.0 g of anhydrous oxalic acid in 160 ml of water at room temperature. Solution 2 was prepared by dissolving 35.6 g of ammonium heptamolybdate, 6.9 g of ammonium metavanadate and 5.8 g of telluric acid ($Te(OH)_6$) in 200 ml of water at 70° C. 7.0 g of concentrated nitric acid was then added to solution 2. The 2 solutions were combined which yielded an orange gel-like precipitate. The mixture was spray dried with the aid of a Buchi-290 spray drier.

The dried material was further dried in static air at 120° C. for 16 hours, milled to a fine powder and then calcined in static air at a temperature of 325° C. for 2 hours. After the air calcination, the material was further calcined in a nitrogen ($N_2$) stream at 600° C. for 2 hours. The resulting mixed metal oxide was then mixed with silica in a weight ratio of 80:20 (weight ratio of mixed metal oxide to silica).

After said mixing, a mixture of 0.6 wt. % Walocel in water and a Binzill CC301 suspension were slowly added to the solid mixture in a Retsch mixer. After mixing and compacting, the mixture was extruded into trilobe shaped bodies, followed by a final calcination in static air at a temperature of 325° C. for 2 hours.

The calcined extrudates were then milled. The milled material was then sieved using a sieve having a mesh size of 40-80 mesh. The sieved material having a size of 40-80 mesh was then used in the ethane oxidative dehydrogenation experiments described below.

(B) Catalytic Oxidative Dehydrogenation of Ethane

The catalyst thus prepared was used in experiments involving ethane oxidative dehydrogenation (ethane ODH) within a small-scale testing unit comprising a vertically oriented, cylindrical, quartz reactor having an inner diameter of 4 mm. 1.60 g of the catalyst was loaded in the reactor. The catalyst bed height was 17 cm. On top of the catalyst bed, another bed having a height of 8 cm was placed which latter bed contained inert silicon carbide (SiC) particles having an average diameter of 0.8 mm.

In these experiments, a gas stream comprising ethane, oxygen ($O_2$) and nitrogen ($N_2$) was fed to the top of the reactor and then sent downwardly through the catalyst bed to the bottom of the reactor. After 120 hours, water was also fed to the top of the reactor. The water was fed to the reactor in the gas phase (as steam). The pressure in the reactor was 4.7 bara. In Table 1 below, the catalyst temperature, the composition of the feed stream to the reactor and the gas hourly space velocity (GHSV) in time periods A to D are shown. By said catalyst temperature, reference is made to the average of the top catalyst temperature and the bottom catalyst temperature, wherein the top catalyst temperature is the temperature measured in the catalyst bed at a position which is about 0.5 cm from the top and the bottom catalyst temperature is the temperature measured in the catalyst bed at a position which is about 0.5 cm from the bottom.

In Table 1, "Nl" stands for "normal litre" as measured at standard temperature and pressure, namely 32° F. (0° C.) and 1 bara (100 kPa). Further, in Table 1, the following parameters are included: 1) molar ratio of water as fed to the reactor to oxygen as fed to the reactor; 2) total amount of water and oxygen as fed to the reactor, based on total amount of components as fed to the reactor; and 3) molar ratio of total amount of oxygen and water as fed to the reactor to ethane as fed to the reactor.

TABLE 1

| | Time period | | | |
|---|---|---|---|---|
| | A | B | C | D |
| Time on stream (TOS; hr) | 0-24 | 24-48 | 48-120 | 120-191 |
| Catalyst temperature (° C.) | 300 | 320 | 340 | 340 |
| Flow $N_2$ (Nl/hr) | 0.77 | 0.77 | 0.77 | 0.77 |
| Flow $O_2$ (Nl/hr) | 0.9 | 0.9 | 0.9 | 0.9 |
| Flow ethane (Nl/hr) | 3 | 3 | 3 | 3 |
| Flow water (Nl/hr) | 0 | 0 | 0 | 0.45 |
| GHSV (Nl/l catalyst/hr) | 2248 | 2248 | 2248 | 2467 |
| Flow $N_2$ (vol. %) | 16.5 | 16.5 | 16.5 | 15.0 |
| Flow $O_2$ (vol. %) | 19.3 | 19.3 | 19.3 | 17.6 |
| Flow ethane (vol. %) | 64.2 | 64.2 | 64.2 | 58.6 |
| Flow water (vol. %) | 0 | 0 | 0 | 8.8 |
| Molar ratio of flow water to flow $O_2$ | — | — | — | 0.5:1 |
| Total of flow water + flow $O_2$ (vol. %) | — | — | — | 26.4 |
| Molar ratio of [total of flow water + flow $O_2$] to flow ethane | — | — | — | 0.5:1 |

In time periods C and D, the conversions of ethane and oxygen and the product composition were measured with a gas chromatograph (GC) equipped with a thermal conductivity detector (TCD) and with another GC equipped with a flame ionization detector. Acetic acid by-product and water from the reaction were trapped in a quench pot.

In the above-described experiments, it has appeared that in time period C, during which period no water was fed to the reactor but only nitrogen, oxygen and ethane, the conversion of ethane decreased over time from an initial value of 25% (at TOS=48 hours) to a value of 21% (at TOS=120 hours). A similar trend was observed for the conversion of oxygen which during time period C decreased over time from an initial value of 53% (at TOS=48 hours) to a value of 45% (at TOS=120 hours). Surprisingly, it has appeared that upon starting the feed of water to the reactor at the beginning of time period D (at TOS=120 hours), both the conversion of ethane and the conversion of oxygen were restored to their original levels. Furthermore, surprisingly, it has appeared that during the entire time period D, the levels of the conversion of ethane and the conversion of oxygen remained stable at around 25% and around 53%, respectively. The foregoing demonstrates that by feeding water to the reactor, in addition to oxygen and ethane, wherein only a relatively small amount of water is fed (wherein the molar ratio of water as fed to oxygen as fed was smaller than 1:1), and is then contacted with the catalyst, both the catalyst activity and the catalyst stability over time are improved.

That which is claimed is:

1. A process for the oxidative dehydrogenation of an alkane containing 2 to 6 carbon atoms and/or the oxidation of an alkene containing 2 to 6 carbon atoms, wherein oxygen, water and the alkane and/or alkene are fed to a reactor and are contacted with a mixed metal oxide catalyst containing molybdenum, vanadium, niobium and optionally tellurium in the reactor, and wherein the molar ratio of water as fed to the reactor to oxygen as fed to the reactor is smaller than 1:1 and the conversion of the alkane containing 2 to 6 carbon atoms and/or the alkene containing 2 to 6 carbon atoms is greater than 30%.

2. The process according to claim 1, wherein the molar ratio of water as fed to the reactor to oxygen as fed to the reactor is of from 0.01:1 to smaller than 1:1.

3. The process according to claim 1, wherein the total amount of water and oxygen as fed to the reactor is of from 10 to 80 vol.

4. The process according to claim 1, wherein the molar ratio of the total amount of water and oxygen as fed to the reactor to the alkane containing 2 to 6 carbon atoms and/or the alkene containing 2 to 6 carbon atoms as fed to the reactor is of from 0.01:1 to smaller than 1:1.

* * * * *